United States Patent [19]

Thompson

[11] 4,332,251
[45] Jun. 1, 1982

[54] INSERTION DEVICE

[76] Inventor: James Thompson, Harrods Creek, Ky. 40027

[21] Appl. No.: 206,721

[22] Filed: Nov. 14, 1980

[51] Int. Cl.³ .............................................. A61F 15/00
[52] U.S. Cl. .................................................... 128/263
[58] Field of Search ........................ 128/263, 270, 285

[56] References Cited

U.S. PATENT DOCUMENTS 2,155,285  4/1939  Wilkerson .......................... 128/263
3,005,456 10/1961  Graham, Jr. ........................ 128/285
3,101,714  8/1963  Penksa ................................ 128/285

Primary Examiner—C. Fred Rosenbaum
Attorney, Agent, or Firm—Edward M. Steutermann

[57] ABSTRACT

An insertion device for insertion of a soft deformable tampon made of resiliently deformable material where the insertion device includes a pair of telescoping elements including a first tube and a second tube of lesser diameter to be received in compressed condition within the first tube with an end of the second tube bearing on the innermost end of the tampon and a generally planar flexible, deformable stop means carried by a string means and movable therealong where the string is attached to the innermost end of the tampon, second stop means provided at the opposite end of the string means to prevent release of the first stop means from the string and the first stop means is received in flexed condition within the tube means.

1 Claim, 6 Drawing Figures

INSERTION DEVICE

BACKGROUND OF THE INVENTION

The use of adsorbent tampons of soft deformable materials such as hydrophilic or menesephilic adsorbent devices is well known.

However the use of such devices have recently been linked to a disease known as toxic shock syndrome which primarily affects young women. The exact cause of the disease is not know but it is thought that the linkage is provided by the discovery that tampons provide a culture medium for growth of bacteria leading to toxic shock syndrome.

It has further been suggested that under certain conditions, it is possible for a female utilizing tampons to, having inserted one tampon, insert a second tampon without removing the first, thereby providing additional exposure time for growth of bacteria leading to toxic shock syndrome.

No prior art device is known for preventing the unintentional insertion of a second tampon after a first tampon thereby providing the extended exposure time to facilitate the growth of bacteria.

SUMMARY OF THE INVENTION

The present invention provides a tampon and insertion device therefor and a means for acknowledging the presence of a first tampon to prevent introduction of a second tampon without removal of the first.

More particularly, the present invention provides an insertion device for insertion of a soft deformable tampon made of resiliently deformable material where the insertion device includes a pair of telescoping elements including a first tube and a second tube of lesser diameter to be received in the first tube where the tampon is received in compressed condition within the first tube with an end of the second tube, bearing on the innermost end of the tampon and a flexible, deformable stop means carried by a string means retained by the innermost end of the tampon where a second stop means are provided at the opposite end of the string means to retain the first stop on the string means between the tampon and the second stop, and the first stop means is initially received within the second tube means.

It will be recognized that various other arrangements also within the scope of the present invention will occur to those skilled in the art upon reading of the disclosure set forth hereinafter.

Figure 1:
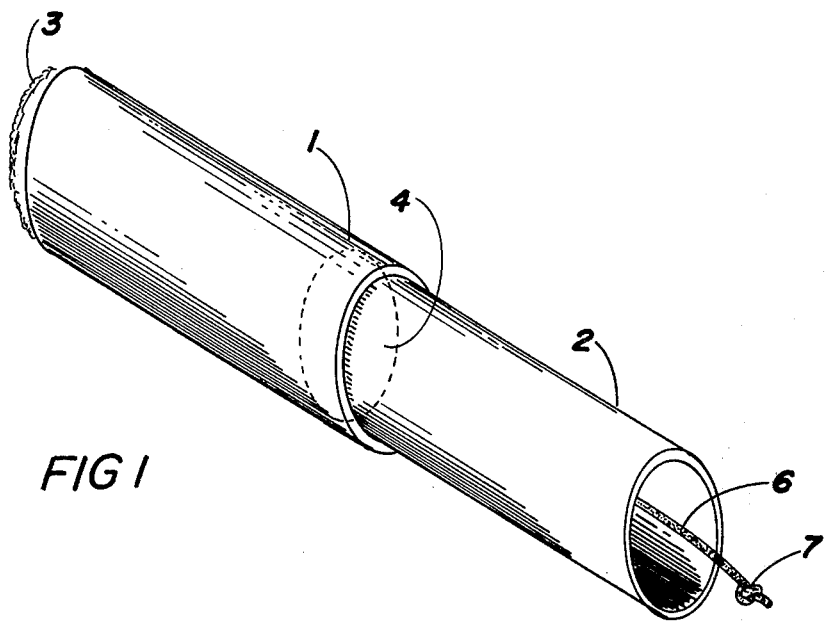
FIG. 1 is a perspective illustration, partially in section of an example of an arrangement within the scope of the present invention.

A device is shown in FIG. 1 in perspective view that includes a pair of telescoping tubular members 1 and 2 where telescoping member 2 is received within member 1 and initially the tampon member 3 is received within member 1 with the innermost end received against the innermost end of member 2.

The delivery system thus comprises a pair of telescoping elements in which the outer element is in the form of a tampon confining tube or sheath and the inner element has a main tubular portion slidably disposed within the outer tube. The structure differs from prior art arrangements in that a preformed deformable flexible disc 4 (shown in shadow line in FIG. 1 is located within tube 2 and retained on a string member 6 having stop or know 7 located in the end thereof. The innermost end of the tampon serves as a bearing surface for the leading end of tube 2 where, as described hereinafter, tube 2 is moved through tube 1 for insertion of the tampon device.

The delivery members 1 and 2 are preferably made of a smooth flexible plastic such as low/hi density polypropylene or polyethylene although other suitable material including other plastics and paperboard may be used. The front of tube 1 may be opened or have substantially closed configuration comprised of adjoining flexible petal shaped elements as are known in the art which flex as the tampon is expelled. The tampon may be made of any soft deformable material but is preferably made of hydrophilic or menesesphilic materials many of which are known in the art such as poloyurthene foam. The tampon may also have various shapes and configurations, the important characteristic is that the selected shape be sufficiently deformable so that when the tampon is located within tube 1 it can easily be emitted from tube 1 and expand as shown in FIGS. 2b-2d and described hereinafter.

Figure 2A:
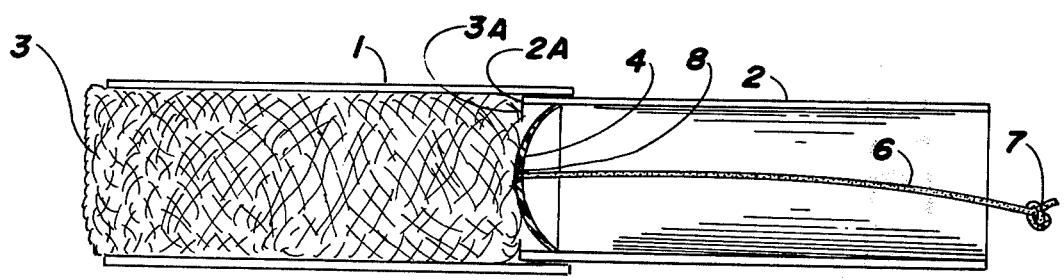
FIGS. 2a-2d illustrate in cross section, the operation of the device shown in FIG. 1.
Figure 2B:
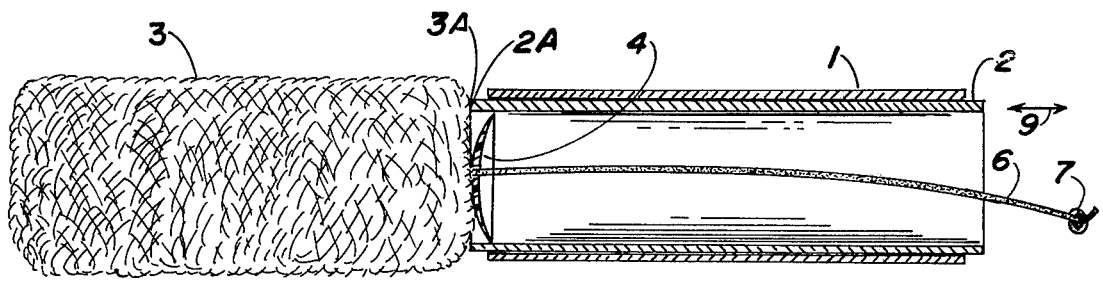
Figure 2C:
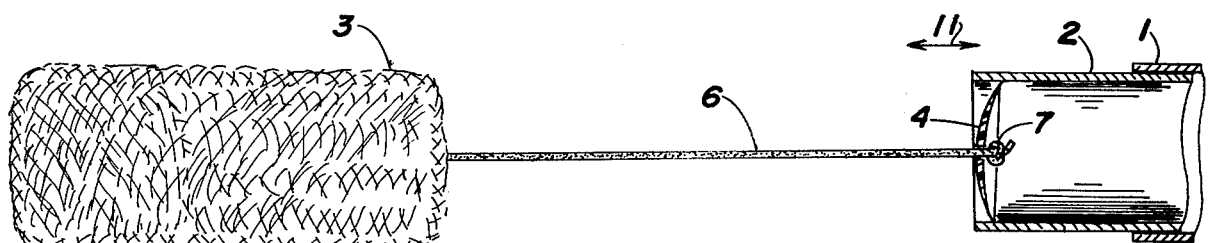
Figure 2D:
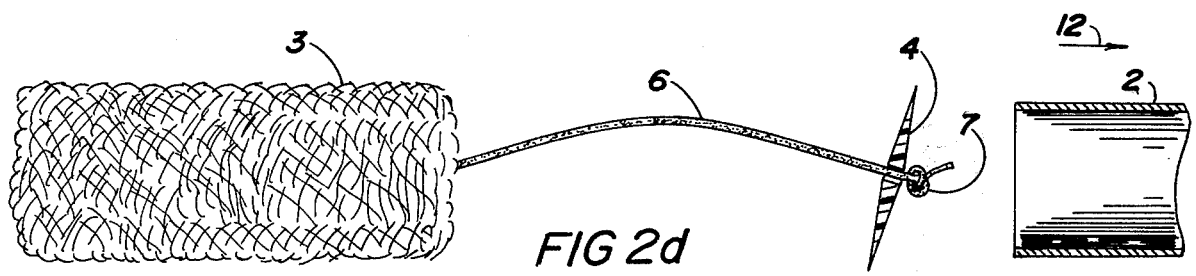

When the tampon and inserter are assembled the tampon may be totally enclosed within the outer tube or alternately may have a portion partially extending out of the front end as shown in FIGS. 1 and 2a as described hereinafter. In the later case the exposed end acts as a swab during insertion and provides added insurance against the possibility of early leaking.

when the tampon and inserter are assembled the tampon may be totally enclosed within the outer tube or alternately may nave a portion partially extending out of the front end as shown in FIG. 1 and 2a as described hereinafter. In the later case the exposed end acts as a swab during insertion and provides added insurance against the possibility of early leaking.

Referring to FIG. 2a which is an illustration of the configuration shown in FIG. 1 in cross section, tampon member 3 can be seen to be disposed within the tube 1 where leading edge 2a of tube 2 bears on the innermost surface 3a of tampon 3.

String 6 is shown, as is disc 4 which is in a flexed state within tube 2 to retain the disc within the tube. A central aperture 8 is provided within disc 4 and string 6 is inserted therethrough to extend from the tampon outwardly from tube 2 and terminate in a stop member, in this case a knot 7.

FIG. 2b is an illustration where tampon 3 has been inserted with the edge 2a of tube 2 shown as the motive force by which the tampon is inserted and tube 3 is moved in the direction indicated by arrow 9. It will be noted that disc 4 is still within tube 2 and is positioned adjacent the end of 3a of tampon 3.

FIG. 2c illustrates the situation where tube 2 has been withdrawn from tube 1 in the direction shown by arrow 11 to the full extent of the length of string 2 such that the stop 7 bears on the inner surface of the disc 4. At this point, flexed disc 4 is about to be released from tube 2.

FIG. 2d is an illustration where disc 4 has been released from tube 2 as tube 2 is moved further in the direction indicated by arrow 12 and where the disc 4 has been released from tube 2, is open, and is in position to indicate the presence of a tampon to avoid the inadvertent insertion of a second tampon without removal of the first.

Figure 3:
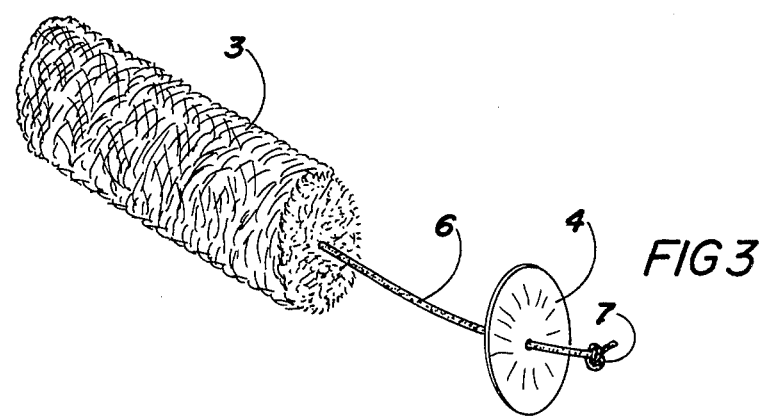
FIG. 3 is a perspective view of one arrangement within the scope of the present invention.

FIG. 3 is a perspective view of the device shown in FIG. 2d to provide a view of the relationship between the tampon 3 in its compressed condition as it is emitted from the tube 1 and the indicator disc 4.

It is to be understood that the foregoing is but one arrangement within the scope of the present invention will occur to those skilled in the art upon reading the disclosure set forth hereinbefore.

I claim:

1. An insertion device for insertion of a soft deformable tampon made of resilient deformable material where the insertion device includes a pair of telescoping elements including a first tube and a second tube of lesser diameter to be received in the first tube where a portion of the tampon is received in compressed condition within the first tube with an end of the second tube, bearing on the innermost end of the tampon and a generally planar flexible, deformable stop means carried by a string means and movable therealong where one end of the string is attached to the innermost end of the tampon, second stop means provided at the opposite end of the string means to prevent release of the first stop means from the string and the first stop means is adapted to be received in flexed condition within the tube means.

* * * * *